(12) United States Patent
Phipps et al.

(10) Patent No.: US 7,054,683 B2
(45) Date of Patent: May 30, 2006

(54) METHODS OF ELECTROTRANSPORT DRUG DELIVERY

(75) Inventors: Joseph B. Phipps, Sunnyvale, CA (US); Gary A. Lattin, Nemo, SD (US); Larry A. McNichols, Elk River, MN (US); John D. Badzinski, Coon Rapids, MN (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 11/214,246

(22) Filed: Aug. 29, 2005

(65) Prior Publication Data

US 2005/0288621 A1    Dec. 29, 2005

Related U.S. Application Data

(63) Continuation of application No. 10/609,211, filed on Jun. 27, 2003, now Pat. No. 6,975,902.

(60) Provisional application No. 60/392,890, filed on Jun. 28, 2002.

(51) Int. Cl.
*A61N 1/30* (2006.01)

(52) U.S. Cl. .................................... 604/20; 604/501
(58) Field of Classification Search ............. 604/20, 604/501, 19.21; 607/115, 152

See application file for complete search history.

(56) References Cited

U.S. PATENT DOCUMENTS

| | | | |
|---|---|---|---|
| 4,383,529 A | 5/1983 | Webster | |
| 4,666,441 A * | 5/1987 | Andriola et al. | 424/448 |
| 4,883,457 A * | 11/1989 | Sibalis | 604/20 |
| 4,917,688 A * | 4/1990 | Nelson et al. | 604/306 |
| 5,053,001 A * | 10/1991 | Reller et al. | 604/20 |
| 5,135,479 A | 8/1992 | Sibalis et al. | |
| 5,320,597 A | 6/1994 | Sage, Jr. et al. | |
| 5,358,483 A | 10/1994 | Sibalis | |
| 5,464,387 A | 11/1995 | Haak et al. | |
| 5,533,995 A | 7/1996 | Corish et al. | |
| 5,583,171 A | 12/1996 | Schwarz et al. | |
| 5,658,247 A * | 8/1997 | Henley | 604/20 |
| 5,865,756 A * | 2/1999 | Peel, III | 600/490 |
| 5,983,131 A * | 11/1999 | Weaver et al. | 604/20 |
| 6,039,977 A | 3/2000 | Venkatraman et al. | |
| 6,393,318 B1 | 5/2002 | Conn et al. | |
| 6,560,483 B1 * | 5/2003 | Kumar et al. | 604/20 |
| 6,975,902 B1 * | 12/2005 | Phipps et al. | 604/20 |
| 2001/0023330 A1 | 9/2001 | Palti | |
| 2002/0107470 A1 * | 8/2002 | Richards et al. | 604/20 |
| 2004/0082901 A1 * | 4/2004 | Phipps et al. | 604/20 |
| 2004/0248320 A1 * | 12/2004 | Santini et al. | 436/174 |

FOREIGN PATENT DOCUMENTS

| | | |
|---|---|---|
| WO | WO 02/074173 | 9/1992 |
| WO | WO 94/01544 | 1/1994 |
| WO | WO92/38198 | 12/1996 |

* cited by examiner

*Primary Examiner*—Sharon Kennedy

(57) ABSTRACT

A reservoir and a family of reservoirs are provided which are designed to be used with a single controller to provide a wide range of therapeutic drug delivering regimens while maintaining many of the same reservoir configurations and drug formulations. A method of making a reservoir and a family of reservoirs and incorporating them into an electrotransport system is disclosed.

19 Claims, 5 Drawing Sheets

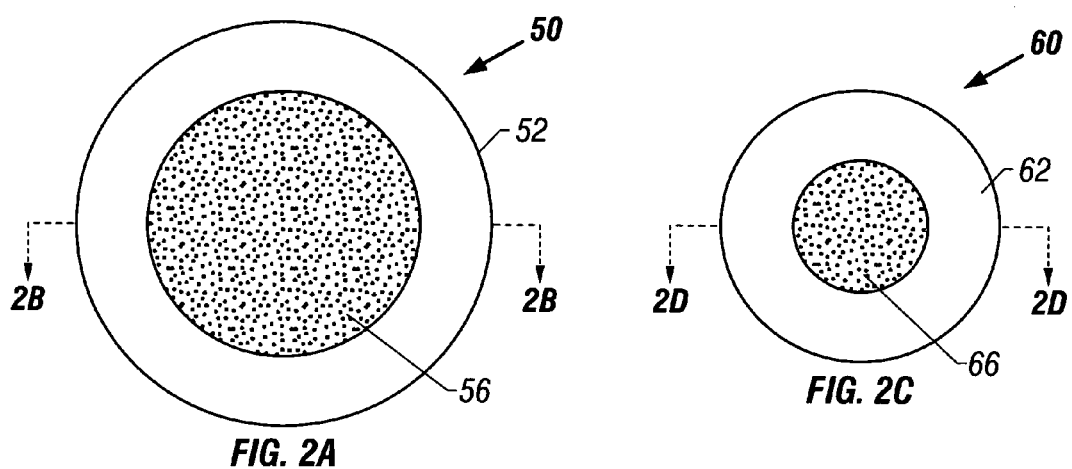
FIG. 2A
FIG. 2C
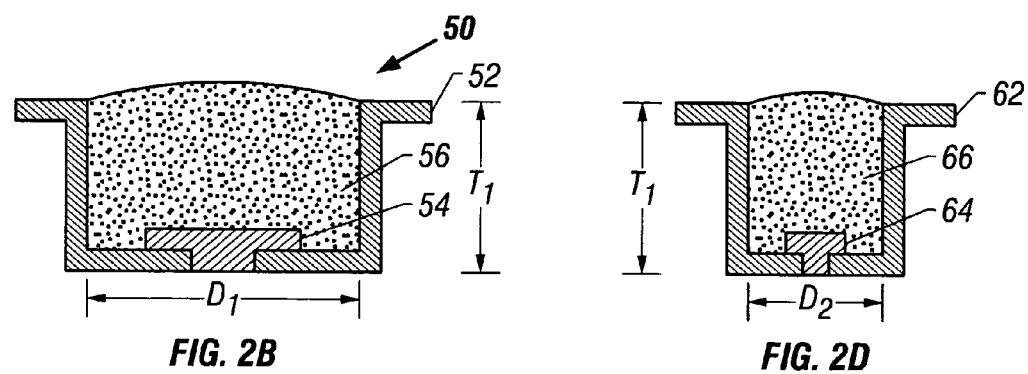
FIG. 2B
FIG. 2D

METHODS OF ELECTROTRANSPORT DRUG DELIVERY

RELATED APPLICATIONS

This application is a continuation of U.S. patent application Ser. No. 10/609,211, filed on Jun. 27, 2003, now U.S. Pat. No. 6,975,902 which is incorporated by reference and which claims benefit from U.S. provisional application Ser. No. 60/392,890 filed 28 Jun. 2002, which is also incorporated herein by reference.

TECHNICAL FIELD

This invention relates generally to electrotransport drug delivery. More particularly, the invention relates to a therapeutic agent-containing reservoir and to an interrelated family of therapeutic agent-containing reservoirs for use in an electrotransport drug delivery device such that each reservoir is capable of delivering a different predetermined dosage of a therapeutic agent. The invention further includes electrotransport devices which are useable with one or more of the reservoirs.

BACKGROUND

The delivery of drugs through the skin provides many advantages. Primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

However, many drugs are not suitable for passive transdermal drug delivery because of their size, ionic charge characteristics and hydrophilicity. One method of achieving transdermal administration of such drugs is the use of electrical current to actively transport drugs into the body through intact skin. The method of the present invention relates to such iontophoresis, which is an example of such an administration technique.

Herein the terms "electrotransport", "iontophoresis", and "iontophoretic" are used to refer to the delivery of pharmaceutically active agents through a body surface by means of an applied electromotive force to an agent-containing reservoir. The agent may be delivered by electromigration, electroporation, electroosmosis or any combination thereof. Electroosmosis has also been referred to as electrohydrokinesis, electro-convection, and electrically induced osmosis. In general, electroosmosis of a species into a tissue results from the migration of solvent in which the species is contained, as a result of the application of electromotive force to the therapeutic species reservoir, which results in solvent flow induced by electromigration of other ionic species. During the electrotransport process, certain modifications or alterations of the skin may occur such as the formation of transiently existing pores in the skin, also referred to as "electroporation". Any electrically assisted transport of species enhanced by modifications or alterations of the body surface (e.g., formation of pores in the skin) are also included in the term "electrotransport" as used herein. Thus, as used herein, the terms "electrotransport", "iontophoresis" and "iontophoretic" refer to (a) the delivery of charged drugs or agents by electromigration, (b) the delivery of uncharged drugs or agents by the process of electroosmosis, (c) the delivery of charged or uncharged drugs by electroporation, (d) the delivery of charged drugs or agents by the combined processes of electromigration and electroosmosis, and/or (e) the delivery of a mixture of charged and uncharged drugs or agents by the combined processes of electromigration and electroosmosis.

Systems for delivering ionized drugs through the skin have been known for some time. British Patent Specification No. 410,009 (1934) describes an iontophoretic delivery device which overcame one of the disadvantages of the early devices, namely, the need to immobilize the patient near a source of electric current. The device was made by forming, from the electrodes and the material containing the drug to be delivered, a galvanic cell which itself produced the current necessary for iontophoretic delivery. This device allowed the patient to move around during drug delivery and thus required substantially less interference with the patient's daily activities than previous iontophoretic delivery systems.

In present day electrotransport devices, at least two electrodes are used simultaneously. Both of these electrodes are disposed so as to be in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the ionic substance to be driven into the body is positively charged, then the positive electrode (the anode) will be the active electrode and the negative electrode (the cathode) will serve as the counter electrode, completing the circuit. If the ionic substance to be delivered is negatively charged, then the cathodic electrode will be the active electrode and the anodic electrode will be the counter electrode.

Existing electrotransport devices additionally require a reservoir or source of the pharmaceutically active agent which is to be delivered or introduced into the body. Such drug reservoirs are connected to an electrode, i.e., an anode or a cathode, of the electrotransport device to provide a fixed or renewable source of one or more desired species or agents. A reservoir would include a reservoir matrix or gel which contains the agent and a reservoir housing which physically contains the reservoir matrix or gel. In addition to the drug reservoir, an electrolyte-containing counter reservoir is generally placed between the counter electrode and the body surface. Typically, the electrolyte within the counter reservoir is a buffered saline solution and does not contain a therapeutic agent. In early electrotransport devices, the donor and counter reservoirs were made of materials such as paper (e.g., filter paper), cotton wadding, fabrics and/or sponges which could easily absorb the drug-containing and electrolyte-containing solutions. In more recent years however the use of such reservoir matrix materials has given way to the use of hydrogels composed of natural or synthetic hydrophilic polymers. See for example, Webster, U.S. Pat. No. 4,383,529 and Venkatraman, U.S. Pat. No. 6,039,977. Such hydrophilic polymeric reservoirs are preferred from a number of standpoints, including the ease with which they can be manufactured, the uniform properties and characteristics of synthetic hydrophilic polymers, their ability to quickly absorb aqueous drug and electrolyte solutions, and the ease with which these materials can be handled during manufacturing. Such gel materials can be manufactured to have a solid, non-flowable characteristic. Thus, the reservoirs can be manufactured having a predetermined size and geometry.

Generally, the geometry of a reservoir can be described in terms of three parameters:

(1) the average cross-sectional area of the reservoir ("$A_{RES}$"), defined as the arithmetic mean of reservoir cross-sectional areas measured at a number of different distances from and parallel to the body surface;

(2) the average thickness of the reservoir; and (3) the body surface contact area ("$A_{BODY}$").

References to reservoir housing configuration and the above parameters include not only the parameters of the physical reservoir housing, but also include the physical parameters of the reservoir gel or matrix as well.

Electrotransport drug delivery devices having a reusable controller designed to be used with more than one drug-containing unit have been described. The drug-containing unit can be disconnected from the controller when the drug becomes depleted and a fresh drug-containing unit can then be connected to the controller. The drug-containing unit includes the reservoir housing, the reservoir matrix, and associated physical and electrical elements which enable the unit to be removably connected, both mechanically and electrically to the controller. In this way, the relatively more expensive hardware components of the device (e.g., the batteries, the light-emitting diodes, the circuit hardware, etc.) can be contained in the reusable controller. The relatively less expensive donor reservoir and counter reservoir may be contained in the single use, disposable drug containing unit. See, Sage et al., U.S. Pat. No. 5,320,597; Sibalis, U.S. Pat. Nos. 5,358,483 and 5,135,479. Electrotransport devices having a reusable electronic controller with single use/disposable drug units have also been proposed for electrotransport systems comprised of a single controller adapted to be used with a plurality of different disposable drug units. For example, Johnson et al., WO 96/38198 discloses the use of such reusable electrotransport controllers which can be connected to drug units for delivering the same drug, but at different dosing levels, (e.g., a high dose drug unit and a low dose drug unit) which can be connected to the same electrotransport controller. Although these systems go far in reducing the overall cost of transdermal electrotransport drug delivery, further cost reductions are needed in order to make this mode of drug delivery more competitive with traditional delivery methods such as by disposable syringe.

DESCRIPTION OF THE INVENTION

The present invention provides a method of modifying the geometry of therapeutic agent-containing reservoirs to create a family of reservoir configurations. This modification is accomplished by altering the three reservoir parameters described above. The actual drug formulation used for the reservoir composition for each reservoir in the family is the same. Only the reservoir geometry is modified to achieve desired performance characteristics.

The present invention includes a method of making both reservoirs and electrotransport systems in which the reservoirs have been modified individually and as part of a family of reservoirs based upon the method modification of the reservoir parameters as described herein.

The present invention further provides a method of varying the electrode area ("$A_{ELECTRODE}$") in conjunction with other reservoir parameters in order to design a reservoir configuration best suited for a particular purpose.

Accordingly, it is a primary aspect of the invention to provide a family of therapeutic agent-containing reservoirs, each having different reservoir parameters but the same reservoir drug composition, for use in an electrotransport drug delivery device. It is another aspect of the invention to provide an electrotransport system that includes at least one of reservoir of such a family of reservoirs.

In accordance with one embodiment of the invention, an electrotransport system for delivering a therapeutic agent transdermally is provided. The system is comprised of an electronic controller which contains an electronic circuit for controlling, and optionally supplying, the electrotransport current applied by the system. Also included is a family of at least two different therapeutic agent-containing units, each of the two units being electrically connectable to the controller to form a complete electrotransport delivery device. Each of the two units has a therapeutic agent-containing reservoir with a drug reservoir composition, an average thickness, and an average cross-sectional area ($A_{RES}$) that is measured in a plane that is roughly parallel to the body surface through which the agent is to be delivered, and an $A_{BODY}$ this the same as the $A_{RES}$ unless the $A_{BODY}$ has been reduced by the use of a mask.

All of the following discussions regarding a family of reservoirs make reference to two drug reservoirs. However, it should be understood that a family of reservoirs can be comprised of any number of drug reservoirs, each one meeting the configuration requirements for that embodiment.

A first embodiment of the invention has the following configuration:

a. the reservoir thickness of each of the two different agent-containing units is the same;

b. the reservoir composition of each of the two different agent-containing units is the same; but c. the average cross-sectional area ($A_{RES}$) of one reservoir is substantially different than the average cross-sectional area of the other reservoir.

Thus, the unit having the reservoir with the substantially smaller average cross-sectional area would be a slower delivering drug unit whereas the unit having the larger average cross-sectional area would be a faster delivering drug unit.

The current supplied by the controller to each different drug reservoir may need to be altered in order to provide the proper current density which varies with the $A_{BODY}$. The means for making such alterations and for recognizing which drug unit is attached to the controller are known to one skilled in the art.

A second embodiment of the invention has the following configuration:

the average cross-sectional areas of the reservoirs in the two agent-containing units are the same, the agent reservoir compositions of the two different agent-containing units are the same, but the thickness of one of the two reservoirs in the agent-containing unit is substantially different than the thickness of the reservoir in the other agent-containing unit.

The two units would deliver at initially the same rate. However, the unit with the thinner reservoir would deliver for a shorter period of time and thus be a low dose unit and the reservoir having the thicker reservoir would deliver for a longer period of time and be a high dose drug unit.

It will be appreciated that the agent reservoir compositions in both of the two above-described embodiments are the same for each of the two different drug units. A number of issues have to be considered when developing different composition, even if these compositions are somewhat similar. Thus it is best to avoid developing more compositions than are needed. Thus, the cost of developing an electrotransport delivery device for delivering a drug at different dosing levels (e.g., high dose and low dose), is substantially reduced since only a single agent reservoir composition is required to be developed.

The invention has particular utility in those electrotransport systems having an electronic controller with an operational life that is substantially longer than the operational life of the therapeutic agent-containing unit (e.g., an electrotransport system comprised of a reusable electronic controller which is adapted to be connected, sequentially, with a plurality of single use/disposable drug units).

In one embodiment, an agent-containing reservoir for incorporation into an electrotransport drug delivery system is provided. The reservoir has been configured to optimize drug delivery, biocompatibility, and electrochemistry. The reservoir is adapted to be placed in agent-transmitting contact with a subject body surface for delivering the agent through the body surface by means of an electrotransport current (i) applied to the reservoir via a reservoir-contacting electrode. The reservoir thus provided is permeable to electrically assisted electrotransport of the agent and has:

a predetermined volume that holds a quantity of the agent sufficient to achieve therapeutically effective delivery of the agent during the entire intended duration of use, wherein the predetermined volume for a given reservoir thickness is defined by the reservoir average cross-sectional area $A_{RES}$ and the thickness of the reservoir;

a surface that is placed in contact with the body of the subject during use, the body-contacting surface having an area $A_{BODY}$ that provides at least one, and preferably all, of:

(i) a reservoir/body surface current density, $I_{BODY}$ ($I_{BODY}$=i/$A_{BODY}$) greater than a critical current density level as defined herein, and (ii) a drug flux j that is biocompatible;

(c) a surface in contact with the electrode, the electrode-contacting surface having an area $A_{ELECTRODE}$ that provides a reservoir/electrode current density $I_{ELECTRODE}$, wherein $I_{ELECTRODE}$=i/$A_{ELECTRODE}$, that results in at least one of:

(i) a desired electrochemical reaction along the electrode-contacting surface, and (ii) avoidance of undesired polarization along the electrode-contacting surface;

and wherein $A_{BODY}$ and $A_{RES}$ may be different.

One embodiment would comprise a system of drug containing units in which the reservoir $A_{RES}$ varies but in which the $A_{BODY}$ is altered to be the same by the use of different sized masks. This enables identical drug delivery but different sized reservoirs (assuming constant current).

In another embodiment, an electrotransport system for delivering an agent through a body surface is provided. The system comprises at least two different types of agent-containing units and a controller. The different agent-containing units contain different amounts of a single formulation of the therapeutic agent to achieve different dosing levels. Each of the reservoirs in the different types of agent-containing units have:

(a) a predetermined volume, (b) a surface that is placed in contact with a body surface of a subject during use, (c) a surface which is in contact with the electrode, and (d) a reservoir average cross-sectional area $A_{RES}$, as described above, wherein $A_{BODY}$ and $A_{RES}$ are different between the distinct agent-containing unit types.

The controller generates and/or controls an electrotransport current (i) and is adapted to be sequentially and removably attachable to a series of agent-containing units, one agent-containing unit at a time. The controller applies the electrotransport current (i) to respective reservoirs in the different types of agent-containing units via a reservoir-contacting electrode.

The system may further comprise a coupler for separably coupling the controller to any one agent-containing reservoir and providing electrical and mechanical connection of the controller to the agent-containing reservoir. The controller may be capable of providing a single current output or multiple current outputs. According to certain embodiments, different types of therapeutic agent-containing reservoirs provide a signal to the controller related to the dosage of the therapeutic agent to be delivered. The controller may include a receiving means for receiving the signal and selecting the output of the controller in response to the signal. The signal may include an optical signal. The signal may include a coded signal from an electro-mechanical connector, the electro-mechanical connector functioning to mechanically and electrically couple the therapeutic agent-containing reservoir to the controller. In some embodiments, the controller may include a capacitance sensor which senses a capacitance signal provided by the therapeutic agent-containing reservoir.

Additional aspects, advantages and novel features of the invention will be set forth in part in the description which follows, and in part will become apparent to those skilled in the art upon examination of the following, or may be learned by practice of the invention.

BRIEF DESCRIPTION OF THE FIGURES

The two reservoirs in FIGS. 2A, 2B and 2C, 2D depict a variable-$A_{RES}$, variable-$A_{BODY}$, and constant-thickness reservoir family. FIGS. 2A and 2B are respectively top-plan and cross-sectional views of the first reservoir having a thickness $T_1$ and relatively large $A_{RES}$ and $A_{BODY}$. FIGS. 2C and 2D are respectively top-plan and cross-sectional views of the second reservoir also having the same thickness $T_1$ as FIGS. 2A and 2B, but a relatively small $A_{RES}$ and $A_{BODY}$. The relatively large diameter of the reservoir and body contact area are shown in FIGS. 2A and 2B and are indicated as $D_1$. The relatively small diameter of the reservoir and body contact area are shown in FIGS. 2C and 2D and are indicated as $D_2$.

The two reservoirs in FIGS. 3A, 3B and 3C, 3D depict a variable-thickness, constant-$A_{RES}$ and constant-$A_{BODY}$ family of reservoirs.

MODES FOR CARRYING OUT THE INVENTION

Figure 1:
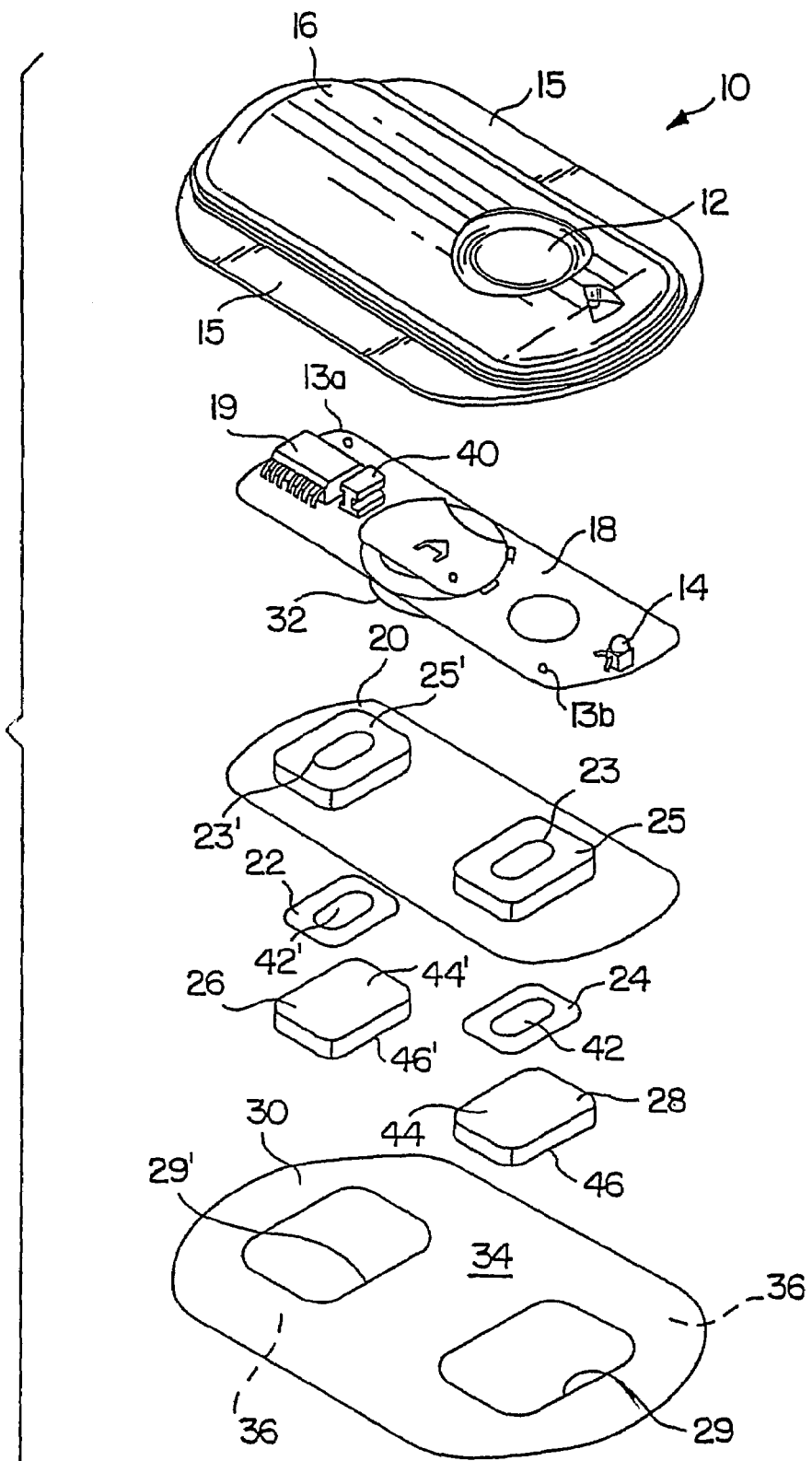
FIG. 1 is a perspective exploded view of one embodiment of an electrotransport drug delivery system which may be used in conjunction with a reservoir according to the present invention.

Before describing the present invention in detail, it is to be understood that this invention is not limited to particular drugs, drug salts, resins, reservoirs or electrotransport delivery systems, as such may vary.

It must be noted that, as used in this specification and the appended claims, the singular forms "a", "an" and "the" include plural referents unless the content clearly dictates otherwise. Thus, for example, reference to "a reservoir" includes one or more reservoirs, reference to "a drug" or "a therapeutic agent" includes a mixture of two or more drugs or agents, reference to "a filler material" includes reference to one or more filler materials, and the like.

In describing and claiming the present invention, the following terminology will be used in accordance with the definitions set out below.

The term "current" or "i" is intended to include both constant current, continuously varying current, and pulsed current, e.g., a square wave current alternating between an "off" state and an "on" state, wherein each "on" state may be constant, varying, greater than, less than or the same as the previous "on" state. Preferably, the current is a constant non-varying DC current or a pulsed DC current in which "on" states are the same constant current.

A "biocompatible" $I_{BODY}$ is a current density less than or equal to the maximum current density that can be tolerated by a patient or subject, e.g., less than that which produces intolerable sensation, skin irritation or damage. In the context of the invention disclosed herein, a biocompatible $I_{BODY}$ is less than or equal to the maximum $I_{BODY}$ that causes a tolerable degree of sensation and/or irritation. In addition, a biocompatible $I_{BODY}$ is one which effectuates sufficient drug delivery to achieve a therapeutic effect, yet less drug delivery than that which would be toxic to the patient or subject. The biocompatibility of $I_{BODY}$ depends on a number of factors, including the nature of the therapeutic agent, the level of current applied to effect delivery, the duration of drug delivery, and the like. Using standard toxicological and clinical methods, a person having ordinary skill in the art will be able to determine what a biocompatible $I_{BODY}$ would be for a particular application. A biocompatible $I_{BODY}$ is typically less than about 0.2 mA/cm$^2$, preferably less than about 0.1 mA/cm$^2$, for chronic drug delivery, e.g., over a period of approximately 12 to 72 hours. For acute drug delivery $I_{BODY}$ is typically less than about 1 mA/cm$^2$, preferably less than about 0.3 mA/cm$^2$. Drug flux is defined as the amount of drug delivered per unit of body surface area per unit time. Accordingly, a biocompatible drug flux j is the flux produced by a biocompatible $I_{BODY}$ and that is within a dosage range that produces a therapeutic effect.

The term "mask" is intended to mean a device which can be used to modify the body surface contact area, $A_{BODY}$, of an agent-containing reservoir. Thus, a mask may include any material that is essentially electrically impermeable and thus restricts the area that current can flow to that portion of the $A_{RES}$ that is not covered by the mask. Preferred materials for the mask include polymeric materials, such as polyesters, polyolefins, polysilicones, polybutylenes, cellulosics, polyvinyl acetates, polycarbonates, and the like. The mask may be a multi-laminate construction having a body surface-contacting adhesive layer.

The term "inert filler material" refers to a material having substantially no tendency to interact with the therapeutic agent or other excipients in the reservoir formulation, which means that such an inert filler material will not bind, absorb, adsorb or react chemically with any significant quantity of therapeutic agent or excipient. In addition, the inert filler will not undergo any substantial electrochemical reaction. The material will generally be particulate or fibrous, or it may be comprised of a glass or ceramic bead, polymeric mesh, gas-filled void, or the like.

By the term "dosage" is meant the amount of agent delivered from an electrotransport delivery device. The term is intended to encompass the amount of drug delivered per unit of time, the total amount of drug delivered over a period of time, the duration of time over which the drug is to be delivered, and the like.

The following synonymous terms, "pharmaceutically active agent", "drug", "agent", or "therapeutic agent", as used herein, mean any chemical material or compound which induces a desired local or systemic effect in a subject, and is capable of being delivered to the subject by electrotransport.

Drugs, which are therapeutic or otherwise are active agents useful in connection with the present invention, include any pharmaceutical compound or chemical that is capable of being delivered by electrotransport. In general, this includes agents in all of the major therapeutic areas including, but not limited to, anti-infectives such as antibiotics and antiviral agents, analgesics including fentanyl, sufentanil, remifentanil, and other opioids, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetics, prostaglandins, psychostimulants, sedatives and tranquilizers. The invention is also useful in conjunction with the electrotransport delivery of proteins, peptides and fragments thereof, whether naturally occurring, chemically synthesized or recombinantly produced.

As noted above, the invention is also useful in the controlled delivery of peptides, polypeptides, proteins and other such species. These substances typically have a molecular weight of at least about 300 daltons, and more typically have a molecular weight of at least about 300 to 40,000 daltons. Specific examples of peptides and proteins in this size range include, without limitation, LHRH, LHRH analogues such as goserelin, buserelin, gonadorelin, napharelin and leuprolide, GHRH, GHRF, insulin, insultropin, calcitonin, octreotide, endorphin, TRH, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, αANF, growth factors such as growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogues, ANP, ANP clearance inhibitors, angiotensin II antagonists, antidiuretic hormone agonists, bradykinin antagonists, CD4, ceredase, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogues, alpha-1 antitrypsin (recombinant), and TGF-beta.

Additional agents include fentanyl hydrochloride, pilocarpine nitrate, lidocaine hydrochloride, hydrocortisone derivatives, sodium salicylate, acetic acid, fluoride anion, lithium, antibiotics such as penicillin and cephalosporin and dexamethasone sodium phosphate, hydromorphone, diazepam salts, antihypertensive agents, bronchodilator agents, peptide hormone and regulatory agents and proteins.

It will be appreciated by those working in the field that the present reservoir system can be used in conjunction with a wide variety of electrotransport drug delivery systems, as the system is not limited in any way in this regard. For examples of electrotransport drug delivery systems, one can refer to U.S. Pat. No. 5,147,296 to Theeuwes et al., U.S. Pat. No. 5,080,646 to Theeuwes et al., U.S. Pat. No. 5,169,382 to Theeuwes et al., and U.S. Pat. No. 5,169,383 to Gyory et al., as well as to U.S. Pat. Nos. 5,224,927, 5,224,928, 5,246,418, 5,320,597, 5,358,483 and 5,135,479, and UK Patent Application No. 2 239 803.

FIG. 1 illustrates a representative electrotransport delivery device that may be used in conjunction with the present reservoir system. Device 10 comprises an upper housing 16, a circuit board assembly 18, a lower housing 20, anode electrode 22, cathode electrode 24, anode reservoir 26, cathode reservoir 28 and body surface-compatible adhesive 30. Upper housing 16 has lateral wings 15 which assist in holding device 10 on the body surface of a subject, e.g., skin, mucosal tissue, and the like. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19, 40, electrodes 22, 24, and drug reservoirs 26, 28, all of which are integrated into a self-contained unit. The outputs (not shown in FIG. 1) of the circuit board assembly 18 make electrical contact with the electrodes 24 and 22 through openings 23, 23' in the depressions 25, 25' formed in lower housing 20, by means of electrically conductive adhesive strips 42, 42'. Electrodes 22 and 24, in turn, are in direct mechanical and electrical contact with the top sides 44', 44 of drug reservoirs 26 and 28. The bottom sides 46', 46 of drug reservoirs 26, 28 contact the subject body surface through openings 29', 29 in adhesive 30.

Device 10 optionally has a feature which allows the subject to self-administer a dose of drug by electrotransport. Upon depression of push button switch 12, the electronic circuitry on circuit board assembly 18 delivers a predetermined DC current to the electrode/reservoirs 22, 26 and 24, 28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of light-emitting diode (LED) 14 becoming lit and/or an audible sound signal from, e.g., a "beeper." Drug is delivered through the subject's body surface by electrotransport, e.g., on the arm, over the predetermined delivery interval.

Anodic electrode 22 is preferably comprised of silver and cathodic electrode 24 is preferably comprised of silver chloride. Both reservoirs 26 and 28 are preferably comprised of polymer hydrogel materials. Additional components, such as inert fillers, may be added to reservoirs 26 and 28. Electrodes 22, 24 and reservoirs 26, 28 are retained by lower housing 20.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25, 25' and cut to form openings 23, 23'. The assembled device 10 is preferably water resistant (i.e., splash proof) and is most preferably waterproof. The system has a low profile that easily conforms to the body, thereby allowing freedom of movement at, and around, the wearing site. Reservoirs 26 and 28 are located on the body surface-contacting side of the device 10 and are sufficiently separated to prevent accidental electrical shorting during normal handling and use.

Device 10 adheres to the patient's body surface by means of a peripheral adhesive 30 which has upper side 34 and body-contacting side 36. Adhesive side 36 has adhesive properties which assures that device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25, 25' as well as retains lower housing 20 attached to upper housing 16.

Reservoirs 26 and 28 generally comprise a gel with the drug solution uniformly dispersed in at least one of reservoirs 26 and 28. Drug concentrations in the range of approximately $1 \times 10^{-4}$ M to 1.0 M or more can be used, with drug concentrations in the middle portion of the range, i.e., 1 mM to 0.1 M, being preferred. Suitable polymers for the reservoir may comprise essentially any nonionic synthetic and/or naturally occurring polymeric materials. A reservoir which is polar in nature is preferred when the active agent is polar and/or capable of ionization, so as to enhance agent solubility. Optionally, the gel polymer will be water-swellable. Examples of suitable synthetic polymers include, but are not limited to, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly(allyl alcohol). Hydroxyl functional condensation polymers (i.e., polyesters, polycarbonates, polyurethanes) are also examples of suitable polar synthetic polymers. Polar naturally occurring polymers (or derivatives thereof) suitable for use as the gel polymer are exemplified by, but not limited to cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers can also be used for the reservoir provided that the available counterions are either drug ions or other ions that are oppositely charged relative to the active agent.

A reservoir disclosed and claimed herein for use in such a device has a predetermined volume and is designed to contain an amount of an drug sufficient to achieve a therapeutic effect. The total amount of drug, $D_T$, incorporated into a reservoir of the invention may generally be determined using the following relationship:

$$D_T = D_E + D_M + (\text{the greatest of } D_F, D_C \text{ and } D_P).$$

In the above relationship, $D_E$ is the amount of drug needed to achieve a therapeutic effect for a desired period of time. $D_M$ is the amount of drug needed to compensate for engineering uncertainty. Such uncertainty may arise from manufacturing limitations, for example, from weighing ingredients, filling reservoir cavities, and the like. The amount $D_M$ is typically calculated from the drug content specification limit, which is generally in the range of from about ±5% to about ±25% of the $D_T$.

$D_F$ is the amount of drug needed to maintain constant drug flux, i.e., flux independent of the concentration of drug in the reservoir. If, for example, the drug concentration were to drop to a level at which flux is dependent on drug concentration, flux would diminish with drug concentration as drug is depleted from the reservoir with delivery to the subject. Under these circumstances, the current supplied from the battery would have to be increased to maintain a flux rate desired to achieve a therapeutic effect. This would cause not only a more rapid power drain of the source but also an increase in $I_{BODY}$, eventually to a level above biocompatibility. Thus, an additional amount of drug above $D_E$ may be added to insure that the flux is independent of the agent concentration throughout the duration of drug delivery.

$D_C$ is the amount of drug required to maintain conductivity of the drug-containing reservoir. Current-driven electrotransport drug delivery is dependent on ionized species dissolved or dispersed in the reservoir. The conductivity of the reservoir is due, at least in part, to the presence of the ionic species contained therein. If the conductivity were to drop sufficiently due to a decrease in the amount of drug in the reservoir, an increase in voltage would be required to maintain constant current and therefore maintain agent flux at a level needed to achieve the desired therapeutic effect. If the voltage required to maintain the target current exceeds the voltage output capabilities of the controller, then the necessary current level cannot be maintained and the desired flux of agent would not be maintained. Thus, an additional amount of drug $D_C$, in addition to $D_E$, may have to be added to the reservoir to minimize the likelihood that the conductivity of the reservoir would drop below a critical level.

$D_P$ is the amount of additional drug needed to avoid unwanted polarization. In a typical electrotransport drug delivery device, the anode is silver and, during operation of the device, the silver is converted to silver ions that are neutralized by anions, e.g., chloride ions, present in the reservoir or migrating into the reservoir from the body. If the quantity or mobility (in units of velocity per unit electric field strength) of the neutralizing counterions is insufficient, then silver ions may migrate into the reservoir. The presence of the silver ions, in concert with the increased voltage required to overcome such polarization, would change the chemical properties, e.g., the pH, of the reservoir. Such a change in reservoir chemistry may affect the ionic character and/or stability of the drug contained therein and, consequently, its current-driven delivery from the reservoir. Since therapeutic drugs are typically provided in salt form, e.g., as their chloride or hydrochloride salt, an additional amount of drug above $D_E$ may be provided to contribute counterions to the reservoir to neutralize the silver ion formed during operation. In general, $D_P$ is the amount of drug required to maintain the favored electrochemical reaction at the electrode, e.g., $Ag + Cl^- \rightarrow AgCl + e^-$, and to minimize unwanted concentration polarization.

The total amount of drug, $D_T$, that is to be placed in a reservoir provides a constraint on the geometry of the reservoir. The reservoir must have a large enough volume to contain a quantity of drug sufficient to achieve a therapeutic effect over the desired administration period. In addition, a reservoir must be sufficiently thin to be flexible and conform to the body surface with which it is contacted. The reservoir must also be wearable. An electrotransport drug delivery device containing a reservoir that is too thick will be difficult or undesirable to wear and may be dislodged by physical contact when worn. Moreover, if a reservoir is too thin, it will need to have a larger $A_{RES}$ to accommodate a given volume of drug formulation, which may result in a $I_{BODY}$ that is too low for efficient drug delivery. Furthermore, the reservoir must be easily manufactured within predetermined tolerances. The reservoir must be manufactured at a reasonable cost and therefore excessively thick or thin reservoirs may be cost-prohibitive to manufacture. Drug remaining in the reservoir upon completion of the therapeutic treatment period is wasted. A desire to minimize this waste also constrains the reservoir volume. This consideration can be particularly important for an expensive drug, or for a drug having high abuse potential.

The requirement for a physically and chemically stable drug formulation also constrains the reservoir geometry. For example, undesirable precipitation of drug during storage may be minimized by using a reservoir containing a concentration of drug less than that which would otherwise be likely to precipitate.

For a given reservoir thickness, the maximum drug concentration possible will dictate the minimum $A_{RES}$ needed for a specific drug and delivery period. The upper limit of drug concentration will be the highest concentration that can be used without the formation of precipitates under the conditions of use.

If this minimum $A_{RES}$ is too large to achieve a desired current density, $I_{BODY}$, the reservoir thickness may be increased to permit a reduction in $A_{RES}$. However, if increasing the thickness is prohibited by other factors, the contact area between the reservoir and the body ($A_{BODY}$) may be reduced by the use of a mask placed between the reservoir and the body. Such a reduction in the $A_{BODY}$ would result in a higher $I_{BODY}$.

Because $A_{RES}$, $A_{BODY}$, and $A_{ELECTRODE}$ are determined by different factors, design of an electrotransport drug delivery system that simultaneously achieves optimal values for each of these design parameters is difficult. The design challenge is particularly difficult when the thickness of the reservoir is constrained and when the need to minimize residual drug is paramount. The invention disclosed and claimed herein provides specific design features adapted to achieve an optimal balance between the different geometric considerations.

The thickness of a reservoir in accordance with this invention is generally less than 1 cm and preferably less than about 0.5 cm since reservoirs having a thickness greater than 1 cm can more easily be manipulated so that the reservoir has a varying cross-sectional area along its thickness. (For example, a reservoir could be tapered, with one end being larger in area than the other end. Typically, though not necessarily, the smaller end would be the body contacting end. The overall volume can be controlled by adjusting both the larger and the smaller diameter, while the $A_{BODY}$ can be controlled by adjusting only the smaller diameter.) With reservoirs formed of polymeric gel materials, the reservoir thickness cannot be reduced to less than about 0.1 mm due to the difficulty in handling and cutting such thin materials. Accordingly, the reservoirs of this invention will generally be between about 0.1 mm to about 10 mm, preferably about 0.5 mm to about 3 mm. A typical reservoir is 2 mm thick. The total amount of drug-contained in a formulation in a reservoir having a predetermined thickness, will be determined by the concentration of drug in the formulation and the $A_{RES}$.

For drug reservoirs that 1) utilize a given drug-containing formulation, 2) have a predetermined thickness and 3) are designed to contain different total amounts of drug, they must each have a different $A_{RES}$. For example, two reservoirs having the same predetermined thickness but that differ by 10-fold in the total amount of drug contained therein, must have a 10-fold difference in their respective $A_{RES}$. Such differences in $A_{RES}$ may result in differences in $A_{BODY}$, as well as in differences in reservoir/electrode contact surface area ($A_{ELECTRODE}$).

For example, a first reservoir containing a large amount of drug may have an $A_{BODY}$ greater than that of a second reservoir containing a small amount of drug. Thus, for a given drug-delivery current, the first reservoir (larger $A_{BODY}$) may have a commensurately low $I_{BODY}$ that may be below a critical $I_{BODY}$.

At least two current density zones have been recognized: one in which drug delivery is independent of current density; and one in which drug delivery is dependent on current density. In essence, a plot of the rate of delivery per unit current, or Rate/i, versus $I_{BODY}$ would show that Rate/i is highly dependent on the $I_{BODY}$ in the range of about 0 to about 30 $\mu A/cm^2$. Rate/i is moderately dependent on the $I_{BODY}$ in the range of about 40 to about 70 $\mu A/cm^2$ and Rate/i is relatively independent of $I_{BODY}$ in excess of about 70 $\mu A/cm^2$.

This change in Rate/i permits delivery of drug in the higher efficiency state with significantly enhanced efficiency. The terms "Rate/i" and "efficiency of drug delivery" are used interchangeably herein.

The term "higher efficiency state" as used herein means the state of a particular body or skin site in which Rate/i for that body site is at least about 10% and preferably 20% greater than the Rate/i at the same site prior to conversion to the higher efficiency state. The term "greater stability state" as used herein means a state of less variable drug delivery from one of greater variability wherein the variability refers to changes in the Rate/i when plotted against current density. The higher efficiency state is the result of exposure of the site to a $I_{BODY}$ above the critical $I_{BODY}$ for a time period longer than the critical time, $t_c$. Critical $I_{BODY}$ for purposes of increased stability has been found to be as low as about 40 $\mu A/cm^2$.

A "Critical $I_{BODY}$" is a current density level above which Rate/i is approximately maximal and substantially independent of current density occurring at the body-contacting surface during therapeutic use of the device. The Critical $I_{BODY}$ may be that current density which, when delivered for critical time $t_c$, will change or convert the transport efficiency of the body surface through which the ionic species is delivered to a nontransitory state of higher or enhanced Rate/i. Current density and the period of application of this current density are chosen to maintain the higher efficiency species delivery state of the body surface.

The precise $I_{BODY}$ and critical time $t_c$ needed to convert an untreated body surface to a highly efficient state are fairly specific to the drug or therapeutic agent to be delivered. However, for electrotransport delivery of analgesics, for example, a treatment of the body site through which drug is to be delivered for a time period of at least 10 milliseconds to 20 minutes or longer, e.g., 30 minutes, at an $I_{BODY}$ of about 40 $\mu A/cm^2$, preferably at least about 50 $\mu A/cm^2$ and most preferably about 70 $\mu A/cm^2$, appears to convert the body site so treated to a highly efficient state.

The amount of drug required to achieve the predetermined dosage, depends, at least in part, on Rate/i. The Rate/i limits the minimum $I_{BODY}$ that can be used to achieve the predetermined dosage. Thus, during a period when the skin site is in a state of lower drug delivery efficiency, more current may be required to deliver the predetermined dosage of drug. In order to increase the amount of current applied to maintain the dosage, the system can be designed with a larger $A_{BODY}$ while still taking into account the maximum biocompatible $I_{BODY}$. In addition, increased current demand may decrease the life expectancy of the battery. It is preferred that the $I_{BODY}$ be maintained at a level above the critical $I_{BODY}$.

The volume of the reservoir required to contain sufficient drug to achieve this predetermined dosage also depends in part on: (a) the amount of drug required to insure a therapeutic level of drug can be delivered for the duration required; and (b) the concentration of drug that can be dissolved in the reservoir formulation.

The reservoir configuration, i.e., thickness and $A_{RES}$, may be designed, for example, by determining the amount of drug formulation required to support the rate of delivery for a predetermined duration and the volume of the reservoir required to contain that amount of drug. Thus, for a predetermined thickness, the $A_{RES}$ of the reservoir may be calculated based on the volume of the drug reservoir required. If the $A_{RES}$ is greater than the $A_{BODY}$ needed to achieve the critical $I_{BODY}$, a mask may be used to reduce the $A_{BODY}$.

In addition, the $A_{BODY}$ may be determined based on (a) the minimum drug delivery rate that is required to achieve a therapeutic effect, (b) the rate at which the drug can be delivered per unit of current supplied by the controller, and (c) the biocompatible $I_{BODY}$.

FIGS. 2A–2D illustrates a constant thickness $T_1$ reservoir family having a variable $A_{BODY}$, variable $A_{RES}$. In FIGS. 2A and 2B, reservoir 50 has a housing 52 that defines the shape of the reservoir and contains electrode 54 and drug-containing gel 56. FIGS. 2C and 2D reservoir 60 has a housing 62 that defines the shape of the reservoir and contains electrode 64 and drug-containing gel 66.

In FIGS. 2A and 2B, reservoir 50 has a larger $A_{BODY}$ and $A_{RES}$ relative to that of reservoir 60 as illustrated in FIGS. 2C and 2D. For reservoir 50, $A_{BODY}$ and $A_{RES}$ are the same, each being circular in shape and having a diameter of $D_1$. For reservoir 60, $A_{BODY}$ and $A_{RES}$ are the same, each being circular in shape and having a diameter of $D_2$, which is smaller than the $D_1$ diameter of reservoir 50. The thickness $T_1$ of reservoirs 50 and 60 are the same as shown in FIGS. 2B and 2D.

The drug containing gel 56 and 66 have the same formulation. However, because of the larger $A_{BODY}$ of reservoir 50, it will deliver drug at a faster rate for any given $I_{BODY}$.

Figure 3A:
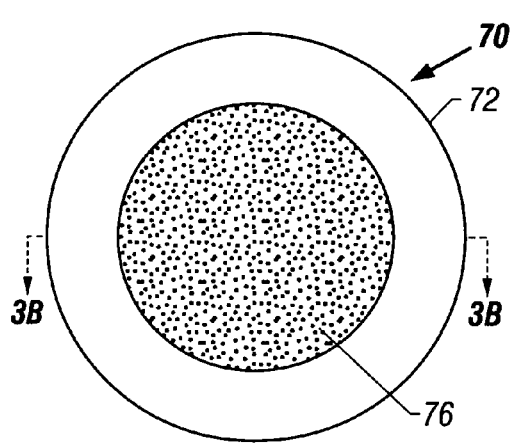
FIGS. 3A and 3B are respectively top-plan and cross-sectional views of the first reservoir having a relatively large thickness $T_2$.
Figure 3C:
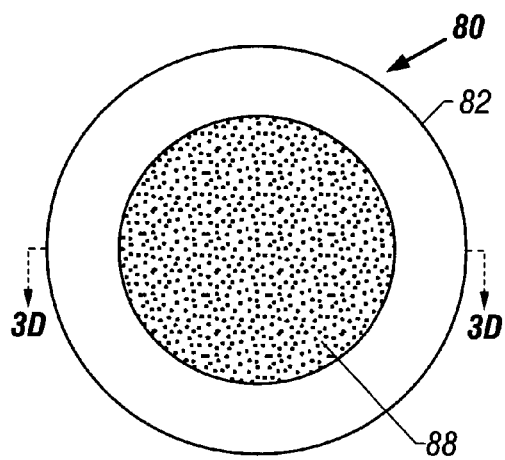
FIGS. 3C and 3D are respectively top-plan and cross-sectional views of such a reservoir having a relatively small thickness $T_3$, and the same $A_{RES}$ and $A_{BODY}$ as shown in FIGS. 3A and 3B.
Figure 3B:
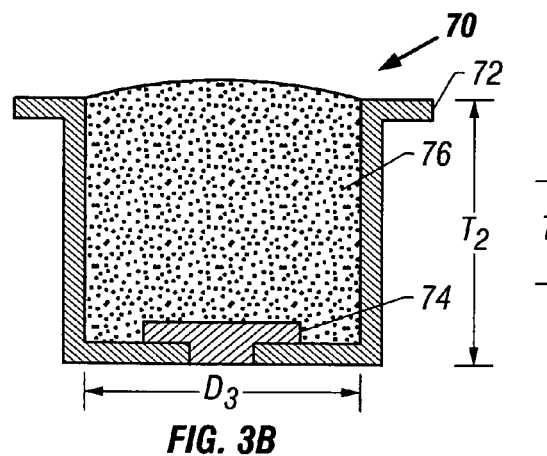
Figure 3D:
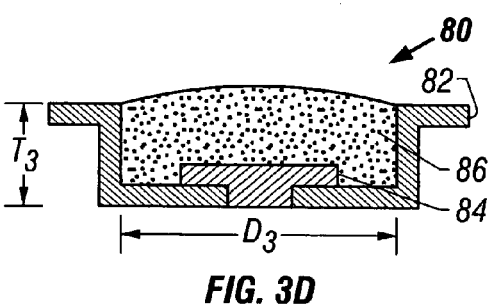

FIGS. 3A–3D illustrate a constant-$A_{BODY}$ and constant-$A_{RES}$ therapeutic agent-containing reservoir family which has a variable thickness. FIGS. 3A and 3B illustrate reservoir 70 having a large thickness $T_2$ relative to thickness $T_3$ of reservoir 80 as shown in FIGS. 3B and 3D. The $A_{BODY}$ and $A_{RES}$ of reservoirs 70 and 80 are circular in shape, have a diameter of $D_3$ and are all of equal size as shown in FIGS. 3A–3D. In these figures, reservoirs 70, 80 have housings 72, 82 that defines the shape of the reservoir and contains electrodes 74, 84 and drug-containing gels 76, 86.

In this family of reservoirs, the initial rate of drug delivery will be the same for reservoirs 70 and 80. However, because of the reduced thickness, $T_3$, of reservoir 80, it contains less volume of gel and a smaller amount drug and will be able to maintain the same drug delivery rate as reservoir 70, but for a much shorter period of time.

Figure 4A:
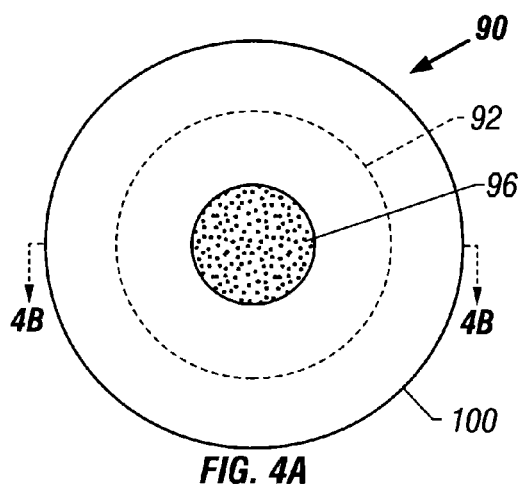
FIG. 4A and FIG. 4B are respectively top-plan and cross-sectional views of a reservoir including an $A_{BODY}$-reducing mask.
Figure 4B:
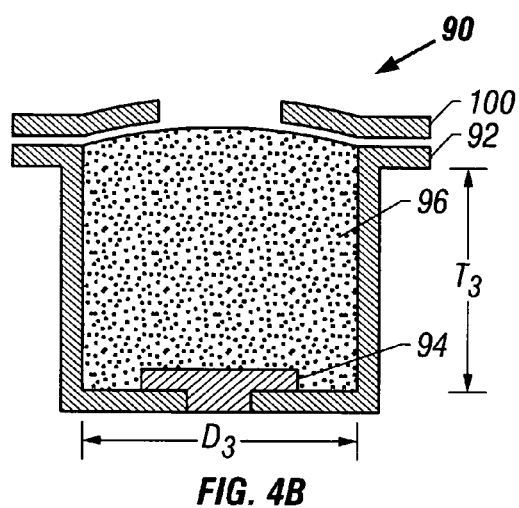

Another alternative embodiment of the invention is illustrated in FIGS. 4A and 4B. Reservoir 90 includes housing 92 that defines the shape of the reservoir and contains electrode 94 and drug-containing gel 96. FIG. 4A and FIG. 4B show reservoir 90 that further includes $A_{BODY}$-reducing mask 100.

Reservoir 70 has the same diameter as reservoir 90 shown in FIGS. 3B and 4B. But because of reducing mask 100, the $A_{BODY}$ and $A_{RES}$ for reservoir 90 are different with $A_{BODY}$ being smaller than $A_{RES}$. Thus with all other factors being the same, including $I_{BODY}$, reservoir 90 will deliver less drug than reservoir 70. It is possible that for reservoir 70, the current density will be less than the critical current density and that for reservoir 90, with the smaller $A_{BODY}$ and the same current, that the current density will be greater than the critical current density. If this is the case, then an enhanced delivery state may occur when reservoir 90 is used and the total drug delivery may be greater than reservoir 70, even with the reduced $A_{BODY}$.

Figure 5:
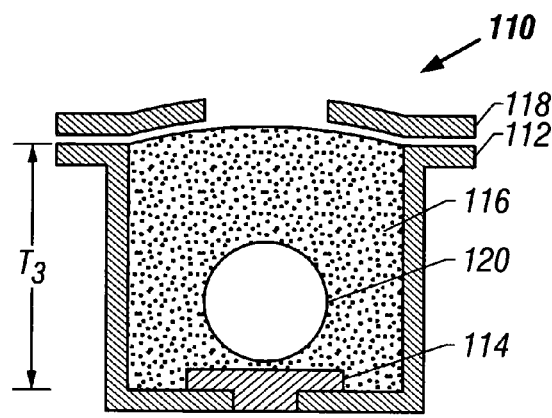
FIG. 5 is a cross-sectional view of a reservoir including an $A_{BODY}$-reducing mask and an inert filler.

An additional embodiment of the invention is illustrated in FIG. 5. FIG. 5 is a cross-sectional view of reservoir 110 that includes housing 112 that defines the shape of the drug reservoir and contains electrode 114, drug-containing gel 116, $A_{BODY}$ reducing mask 118 and inert filler 120. Inert filler 120 is shown in FIG. 5 as a spherical element but can take any convenient form including disks, beads, particles, powder and the like. One purpose of the inert filler is to reduce the volume of drug reservoir 110 without affecting the $A_{RES}$ or thickness thereof. Reservoir 110 is identical to reservoir 90 shown in FIG. 4B, with the exception of the inert filler 120. Thus $A_{RES}$, $A_{BODY}$, and thickness are the same. However, the total volume of gel in reservoir 110 is smaller and therefore reservoir 110 would be able to deliver drug for a shorter period of time when compared to reservoir 90.

The filler may be wax (e.g., paraffin), polytetrafluoroethylene (e.g., Teflon®), or other material that does not adversely affect the integrity of the drug contained in the reservoir or the ability of the device to deliver the drug.

Figure 6:
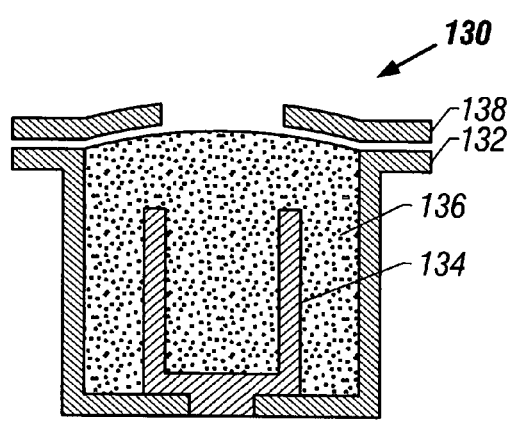
FIG. 6 depicts a reservoir including an $A_{BODY}$-reducing mask and an electrode shaped to provide an increased $A_{ELECTRODE}$.

Materials suitable for use as the inert filler include, but are not limited to: glass beads; mineral filler materials, such as titanium dioxide, talc, quartz powder, or mica; and polymer filler materials. Examples of polymer filler materials are: polymer meshes, such as Saati polypropylene mesh; polymer powders having particle sizes of between about 1 micron to about 50 micorons, such as micronized polymer waxes of polyethylene (e.g., Aqua Poly 250), polypropylene (e.g., Propyltex® 140S), polytetrafluoroethylene (e.g., Fluo 300), Fischer-Tropsch waxes (e.g., MP-22C, available from Micro Powders, Inc.) and mixtures thereof; crosslinked polymer beads, such as styrene/divinylbenzene (e.g., Amberlite® XAD-4 1090 or Amberlite® XAD 16-1090), acrylic/divinylbenzene (e.g., Amberlite® XAD-7) (available from Rohm and Haas), or the like; cellulosic polymers, such as crosslinked dextrans (e.g., Sephadex®) (available from Pharmacia Laboratories); polymer solids having weight average molecular weights between about 20,000 and about 225,000, such as polyvinyl alcohol (e.g., Airvol® 103, available from Air Products; Mowiol® 4-98 and Mowiol® 66-100, available from Hoechst), polyvinylpyrrolidone (e.g., Povidone PVP K-29/32), and mixtures thereof. An additional embodiment of the invention is illustrated in FIG. 6. FIG. 6 is a cross-sectional view of reservoir 130 that includes housing 132 that defines the shape of the drug reservoir and contains electrode 134, drug-containing gel 136, and $A_{BODY}$ reducing mask 138. In this embodiment, electrode 134 functions in a manner similar to the inert filler 120 shown in FIG. 5.

EXAMPLE 1

Determination of Body Surface-Contact Area for Electrotransport Delivery of Fentanyl Results from typical calculations on which reservoir configuration may be based are provided in Table 1 for the drug fentanyl. This table is based upon a family of reservoirs having the same thickness and the same fentanyl reservoir composition.

For example, to achieve a rate of drug delivery of 150 μg/hr for a drug with a Rate/i of 1.1 μg/hr/μA and a $I_{BODY}$ of 75 μA/cm², a body surface-contact area of 1.82 cm² is required.

This is determined by looking down the "Rate" column until the "150" row is found. Then move to the right to the middle of the three major columns corresponding to a Rate/i of 1.1. Then within the three columns under the 1.1 Rate/i column, find the $I_{BODY}$ column corresponding to 75. The value at the intersection of the 150 μg/hr Rate row and the proper column for $I_{BODY}$ and Rate/i is an area of 1.82 cm² for the $A_{BODY}$. Corresponding values can be determined for other values of Rate, Rate/I; and $I_{BODY}$.

If the reservoir thickness is reduced by half, then $A_{RES}$ must be increased two-fold in order to maintain an adequate drug supply. Therefore, to maintain a minimal $I_{BODY}$ of 75 μA/cm², the $A_{BODY}$ would have to be reduced by half by masking off the reservoir, e.g., back to an $A_{BODY}$ of 1.82 cm² for the 150 μg/h system, see Table 1.

TABLE 1

| 72-HOUR CHRONIC FENTANYL ELECTROTRANSPORT SYSTEM | | | | | | | | | |
|---|---|---|---|---|---|---|---|---|---|
| Rate/i ($\mu$g/h/$\mu$A) → | 0.9 | | | 1.1 | | | 1.3 | | |
| $I_{BODY}$ ($\mu$A/cm$^2$) → | 50 | 75 | 100 | 50 | 75 | 100 | 50 | 75 | 100 |
| Rate ($\mu$g/hr) ↓ | $A_{BODY}$ (cm$^2$) | | | | | | | | |
| 25 | 0.56 | 0.37 | 0.28 | 0.45 | 0.30 | 0.23 | 0.38 | 0.26 | 0.19 |
| 50 | 1.11 | 0.74 | 0.56 | 0.91 | 0.61 | 0.45 | 0.77 | 0.51 | 0.38 |
| 75 | 1.67 | 1.11 | 0.83 | 1.36 | 0.91 | 0.68 | 1.15 | 0.77 | 0.58 |
| 100 | 2.22 | 1.48 | 1.11 | 1.82 | 1.21 | 0.91 | 1.54 | 1.03 | 0.77 |
| 150 | 3.33 | 2.22 | 1.67 | 2.73 | 1.82 | 1.36 | 2.31 | 1.54 | 1.15 |

Using a constant $A_{BODY}$ of 1.82 cm$^2$, the thickness of the reservoir is controlled by the amount of drug required to provide a predetermined dosage and consequentially by the volume of the reservoir required to contain the required amount of drug.

As shown in Table 1, the $A_{BODY}$ for a given Rate/i is directly proportion to the desired rate of drug delivery. Thus, an electrotransport drug delivery device can be designed comprising a plurality of drug-containing reservoirs each having the same thickness and a $A_{BODY}$ designed to accommodate a quantity of drug sufficient to achieve a therapeutic effect. The $A_{BODY}$ may be selected to achieve the predetermined dosage at the desired current density using a mask.

EXAMPLE 2

Determination of Electrode Contact Area for Electrotransport Delivery of Fentanyl The electrode-reservoir contact surface area ("$A_{ELECTRODE}$") may be determined based on three parameters:
a. agent delivery per unit current (which is a property of the agent);
b. the desired electrode current density, $I_{ELECTRODE}$; and
c. the desired agent delivery rate.

Table 2 illustrates how these parameters determine the required $A_{ELECTRODE}$ for fentanyl. The $I_{ELECTRODE}$ values in Table 2 differ from the $I_{BODY}$ values provided for fentanyl in Table 1. This is due to the different requirements for reliable electrochemical operation at the electrode/gel interface from those requirements for the gel/skin interface.

The choice of $I_{ELECTRODE}$ is also influenced by the drug composition and the drug formulation in the reservoir. For example, as the $A_{RES}$ is decreased to ate a particular volume of drug formulation, the $A_{ELECTRODE}$ may be reduced as an amount of current required to deliver an agent at a predetermined rate, the $I_{ELECTRODE}$ will increase as the $A_{ELECTRODE}$ decreases. As the $I_{ELECTRODE}$ increases, the electrochemical reaction that takes place at the electrode-reservoir interface will require more counter ions to prevent silver migration and the oxidation of water in the formulation, which will change the pH of the formulation and the ionic nature of the agent, or oxidation of the agent itself. In order to maintain the $I_{ELECTRODE}$ below a level at which such undesirable side effects may occur, the $A_{ELECTRODE}$ must be maintained above a minimum level. In order to increase the $A_{ELECTRODE}$, the $A_{RES}$ may have to be larger than the $A_{BODY}$ that is required to maintain a minimal $I_{BODY}$. Thus, the reservoir would have to be "masked down" to reduce the $A_{BODY}$ and increase the $I_{BODY}$ above the minimal $I_{BODY}$.

Alternatively, the $A_{ELECTRODE}$ can be increased by using an electrode that is fabricated to have a greater surface area, e.g., having a corrugated surface, or being U-shaped, in which case the electrode would be embedded in the reservoir rather than on the surface thereof (see FIG. 6).

Using an embedded electrode as shown in FIG. 6 is also useful when an overall increase in drug delivery is desired. For example, if the drug delivery rate from a reservoir having the configuration as shown in FIG. 4B were to be increased several fold, the total current i would have to be increased. If no other changes were made, this would result

TABLE 2

| 72-HOUR CHRONIC FENTANYL ELECTROTRANSPORT SYSTEM | | | | | | | | | |
|---|---|---|---|---|---|---|---|---|---|
| Rate/i ($\mu$g/h/$\mu$A) → | 0.9 | | | 1.1 | | | 1.3 | | |
| $I_{ELECTRODE}$ ($\mu$A/cm$^2$) → | 40 | 50 | 75 | 40 | 50 | 75 | 40 | 50 | 75 |
| Delivery Rate ($\mu$g/hr) ↓ | $A_{ELECTRODE}$ (cm$^2$) | | | | | | | | |
| 25 | 0.69 | 0.56 | 0.37 | 0.57 | 0.45 | 0.30 | 0.48 | 0.38 | 0.26 |
| 50 | 1.39 | 1.11 | 0.74 | 1.14 | 0.91 | 0.61 | 0.96 | 0.77 | 0.51 |
| 75 | 2.08 | 1.67 | 1.11 | 1.70 | 1.36 | 0.91 | 1.44 | 1.15 | 0.77 |
| 100 | 2.78 | 2.22 | 1.48 | 2.27 | 1.82 | 1.21 | 1.92 | 1.54 | 1.03 |
| 150 | 4.17 | 3.33 | 2.22 | 3.41 | 2.73 | 1.82 | 2.88 | 2.31 | 1.54 | in an increase in the $I_{ELECTRODE}$, potentially to the level at which undesirable electrochemical reactions would occur at the electrode. This problem can be solved by increasing the $A_{ELECTRODE}$ to a size that the $I_{ELECTRODE}$ falls below the problematic level. The $A_{ELECTRODE}$ can easily be increased by simply increasing its size so that it is the same size as the $A_{RES}$. However, if $A_{ELECTRODE}$ needs to be larger than $A_{RES}$, in order that $I_{ELECTRODE}$ be still smaller, then the electrode will need to project into the reservoir as shown as in FIG. 6.

EXAMPLE 3

Family of Reservoirs having Different Delivery Rates

In the treatment of chronic pain, the phenomenon of required dose-escalation over time in order to alleviate the same level of pain is often experienced by those using narcotic analgesics (e.g., morphine and its analogues, fentanyl and its analogues). This phenomenon requires that the dosage be increased over time to achieve an equivalent degree of pain relief. What is described in this example are two members of a family of two or more reservoirs which provide for identical reservoirs sizes, essentially identical reservoir housings and identical reservoir compositions. This provides an easy way to select a one of several dosage delivery rates by attaching one of the family of reservoirs to the same controller. As will be discussed, the control is a smart controller which recognizes the particular drug reservoir that has been attached to the controller.

Figure 7A:
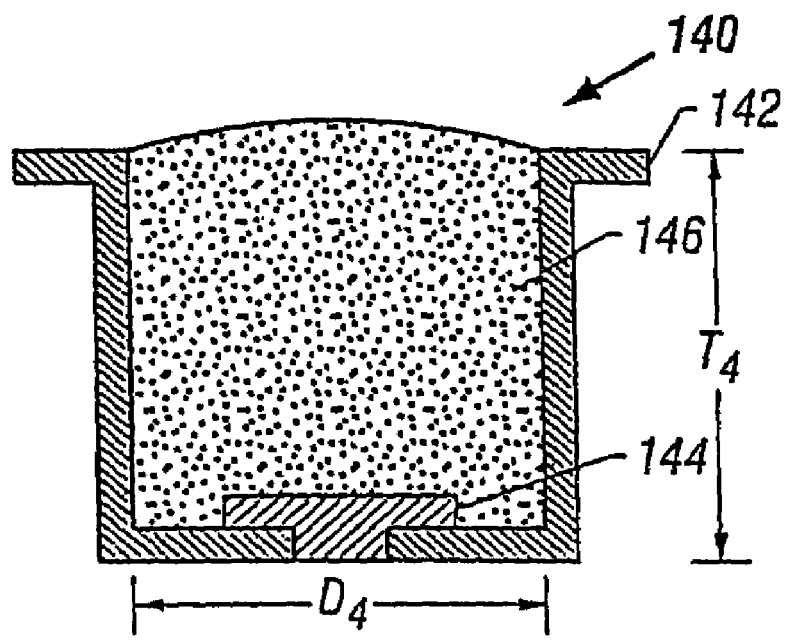
FIGS. 7A and 7B depict two reservoirs from a family of reservoirs which are essentially the same in all physical and chemical parameters, but which provide for varying drug delivery based upon the use of a mask (as shown in FIG. 7b) which decreases the $A_{BODY}$ (Assuming the same $I_d$)
Figure 7B:
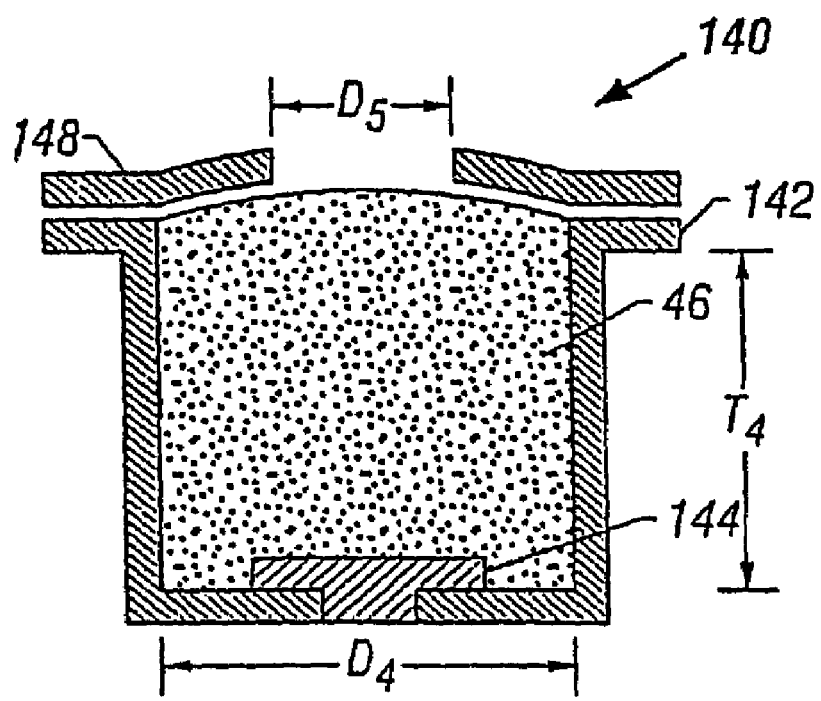

Two members of a family of reservoir are shown in FIGS. 7A and 7B. Each of these two reservoirs is identical in all respects with the exception of Mask 148, which is not present in FIG. 7A and is present in FIG. 7B.

Assuming a typical body current density, $I_{BODY}$, of 100 microamps/cm$^2$, and a body contact area, $A_{BODY}$, of 1 cm$^2$, a current of 100 microamps would be required. If one wanted to decrease the rate of drug delivery, then one could decrease the body contact area, $A_{BODY}$ as long as the $I_{BODY}$ was maintained the same. One way would be to make a reservoir having a smaller $A_{RES}$ and a correspondingly smaller $A_{BODY}$. The drawback to this approach is that a number of other factors would have to be changed including the diameter and thickness of the reservoirs, and all the concomitant changes in manufacturing and assembly that would be required to produce this reservoir. To maintain the same overall drug capacity, the reservoir would have to be thicker to accommodate a greater volume of drug formulation.

An alternative is to utilize the reservoir configuration changes shown in FIG. 7B. In this reservoir, the body contact area, $A_{BODY}$, is reduced by inclusion of Mask 148, which effectively reduces the actual contact area of the reservoir, $A_{RES}$, by masking off a portion of it behind the insulating layer of Mask 148. Other than the inclusion of the mask, the reservoirs of FIGS. 7A and 7B are the same.

Let's assume that Mask 148 in FIG. 7B reduces the contact area by one half. To maintain the $I_{BODY}$ at the desired level of 100 microamps/cm$^2$, the current delivered by the controller must be reduced by half. Though not shown here, there are a number of techniques by which a controller could sense which of several reservoirs was being attached and adjust the current level corresponding to that particular drug reservoir unit.

The great benefit from this system is that a great majority of the physical parameters of the reservoir and the reservoir composition are all the same. This enables the reservoirs to be highly optimized in terms of volume, $A_{RES}$, $A_{ELECTRODE}$, $I_{BODY}$, $I_{ELECTRODE}$, and reservoir formulations, but at the same time provide a series of drug reservoirs from which can be selected the particular reservoir that fits the needs of a particular patient. Although this embodiment has been described with reference to two reservoirs, the inventive concept can, in the same manner, be applied to a family having any number of reservoirs.

Thus, the invention provides a novel therapeutic agent-containing reservoir for use in an electrotransport drug delivery device and a system comprising a plurality of classes of such reservoirs. Although preferred embodiments of the subject invention have been described in some detail, it is understood that obvious variations can be made without departing from the spirit and the scope of the invention as defined by the appended claims.

What is claimed is:

1. A method of varying the delivery rate of a drug comprising:
   providing a plurality electrotransport delivery reservoirs, each reservoir adapted to be placed in drug-transmitting contact with a subject body surface for delivering the drug through the body surface by means of an electrotransport current (i) applied to the reservoir via a reservoir-contacting electrode, the reservoir being permeable to electrically assisted flux of the drug, each of the reservoirs containing the same drug and the geometry of each of the reservoirs being defined by at least three parameters including average cross-sectional area $A_{RES}$, average thickness, and body surface contact area $A_{BODY}$;
   arranging an electronic controller including an electronic circuit adapted to control the electrotransport current applied to the reservoirs so that the controller can be connected to each of the plurality of reservoirs; and
   varying at least one of the parameters for one of the plurality of reservoirs so that the varied parameter is different than the same parameter for another of the plurality of reservoirs such that the delivery rate from one of the plurality of reservoirs is different than the delivery rate of another of the plurality of reservoirs.

2. The method of claim 1, wherein the average thickness of one of the plurality of reservoirs is different from the average thickness of another of the plurality of reservoirs.

3. The method of claim 2, wherein the average cross-sectional area and the body contact surface area of one of the plurality of reservoirs are substantially equal to the average cross-sectional area and the body contact surface area of another of the plurality of reservoirs.

4. The method of claim 2, wherein the average cross-sectional area and the body contact surface area of one of the plurality of reservoirs are different from the average cross-sectional area and the body contact surface area of another of the plurality of reservoirs.

5. The method of claim 1, wherein the body contact surface area for two controllers different and the average cross-sectional area and the average thickness of two controllers is the same.

6. The method of claim 5, wherein body contact surface area of one of the plurality of reservoirs is varied by masking a portion of the one of the plurality of reservoirs intended to contact the body.

7. The method of claim 1, wherein the controller is separably coupleable to at least two of the reservoirs.

8. The method of claim 1, wherein the controller is coupled to one of the plurality of reservoirs at a time.

9. The method of claim 8, wherein the controller is coupled sequentially to each of the plurality of reservoirs.

10. The method of claim 1, wherein the drug includes fentanyl or sufentanil.

11. A method of providing a variety of drug delivery regimens for a drug comprising providing a family of electrotransport delivery reservoirs, each of the reservoirs adapted to be placed in drug-transmitting contact with a subject body surface for delivering the drug through the body surface by means of an electrotransport current applied to the reservoir via a reservoir-contacting electrode, the reservoir being permeable to electrically assisted flux of the drug, each of the reservoirs containing the same drug, wherein one of the reservoirs has a geometrical parameter that is different from the same geometrical parameter of another of the family of reservoirs and connecting each of the family of reservoirs at different times to an electronic controller including an electronic circuit adapted to control the electrotransport current applied to the reservoirs such that the drug delivery regimen from one of the family of reservoirs is different from the drug delivery regimen from another of the family of reservoirs.

12. The method of claim 11, wherein one of the reservoirs includes a mask to reduce the contact area of the reservoir with the body such that the contact area of the masked reservoir is less than the contact area of another of the family of reservoirs.

13. The method of claim 12, wherein the each of the family of reservoirs has the same thickness.

14. The method of claim 13, wherein, the body contact area of each of the family of reservoirs is different and designed to deliver a predetermined dosage at a desired current density to achieve a therapeutic effect.

15. The method of claim 11, wherein the surface area of the reservoir-contacting electrode of at least one of the family of reservoirs is less than the surface area of the reservoir-contacting electrode of another of the family of reservoirs.

16. A method of varying the drug delivery from an electrotransport drug delivery reservoir comprising providing a family of reservoirs, each reservoir adapted to be placed in drug-transmitting contact with a subject body surface for delivering a drug through the body surface by means of an electrotransport current applied to the reservoir via a reservoir-contacting electrode, the reservoir being permeable to electrically assisted flux of the drug, wherein at least two reservoirs have the same geometrical dimensions;

varying the body contact areas of the at least two reservoirs having the same geometrical dimensions by placing a mask over a portion of one of the two reservoirs having the same geometrical dimensions so that application of the same current to the two reservoirs results in a different drug delivery rate from the two reservoirs; and electrically connecting the at least two reservoirs having the same geometrical dimensions to an electronic controller including an electronic circuit adapted to control the electrotransport current applied to the at least two reservoirs.

17. The method of claim 16, wherein the electronic controller is electrically connected at different times to each of the at least two reservoirs having the same geometrical dimensions.

18. The method of claim 17, further comprising electrically connecting each of the at least two reservoirs sequentially.

19. The method of claim 16, wherein the drug includes fentanyl or sufentanil.

* * * * *